(12) United States Patent
Sakamoto et al.

(10) Patent No.: US 7,054,801 B2
(45) Date of Patent: May 30, 2006

(54) RADIATION TREATMENT PLAN MAKING SYSTEM AND METHOD

(75) Inventors: Hidenobu Sakamoto, Tokyo (JP); Yuehu Pu, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 932 days.

(21) Appl. No.: 09/904,889

(22) Filed: Jul. 16, 2001

(65) Prior Publication Data

US 2002/0128807 A1    Sep. 12, 2002

(30) Foreign Application Priority Data

Jan. 23, 2001 (JP) ............... 2001-014870

(51) Int. Cl.
*G06F 17/50* (2006.01)
*G06G 7/62* (2006.01)
*A61N 5/00* (2006.01)
*G21G 5/00* (2006.01)

(52) U.S. Cl. .............. 703/13; 703/11; 250/492.3; 315/501; 315/505

(58) Field of Classification Search ............ 703/11, 703/13; 250/492.3; 315/501, 505
See application file for complete search history.

(56) References Cited

U.S. PATENT DOCUMENTS

| | | | |
|---|---|---|---|
| 5,039,867 A * | 8/1991 | Nishihara et al. | 250/492.3 |
| 5,818,902 A | 10/1998 | Yu | |
| 5,969,367 A * | 10/1999 | Hiramoto et al. | 250/492.3 |
| 6,256,591 B1 * | 7/2001 | Yoda et al. | 702/57 |
| 6,260,005 B1 * | 7/2001 | Yang et al. | 703/11 |
| 6,265,837 B1 * | 7/2001 | Akiyama et al. | 315/503 |
| 6,268,610 B1 * | 7/2001 | Pu | 250/492.3 |
| 6,316,776 B1 * | 11/2001 | Hiramoto et al. | 250/492.3 |
| 6,597,005 B1 * | 7/2003 | Badura et al. | 250/505.1 |
| 2002/0051513 A1 * | 5/2002 | Pugachev et al. | 378/65 |

FOREIGN PATENT DOCUMENTS

| | | | |
|---|---|---|---|
| GB | 2371462 A | * | 7/2002 |
| JP | 3-43904 | | 7/1991 |
| JP | 9-223600 | | 8/1997 |

OTHER PUBLICATIONS

John W. Staples, et al. "Modeling and System Specifications for an Integrated 3-D Proton Treatment Delivery System", 1993 IEEE pp. 1759-1761.

(Continued)

*Primary Examiner*—Paul L. Rodriguez
*Assistant Examiner*—Ayal Sharon
(74) *Attorney, Agent, or Firm*—Oblon, Spivak, McClelland, Maier & Neustadt, P.C.

(57) ABSTRACT

A radiation exposure region to be irradiated with particle beams and a peripheral region thereof are respectively divided into pluralities of exposure regions, radiation treatment simulation for applying particle beams according to the shape of each divided exposure region is performed, and a radiation treatment condition is obtained for causing the flatness of the radiation exposure region to be in a desired range, and a dose of particle beams applied to the unit exposure region of the peripheral region to be minimum. Thus, the problem of low efficiency of radiation is solved.

2 Claims, 8 Drawing Sheets

OTHER PUBLICATIONS

E. Pedroni, "Status of Proton Therapy: results and future trends" Proceedings of NIRS International Seminar on the Application of Heavy Ion Accelerator to Radiation Therapy of Cancer in connection with XXI PTCOG Meeting, Nov. 14-16, 1994, pp. 407-411.

Th. Haberer, et al., Nuclear Instruments and Methods in Physics Research, section A, vol. A330, Nos. 1,2, pp. 296-305, "Magnetic Scanning System for Heavy Ion Therapy", Jun. 10, 1993.

* cited by examiner

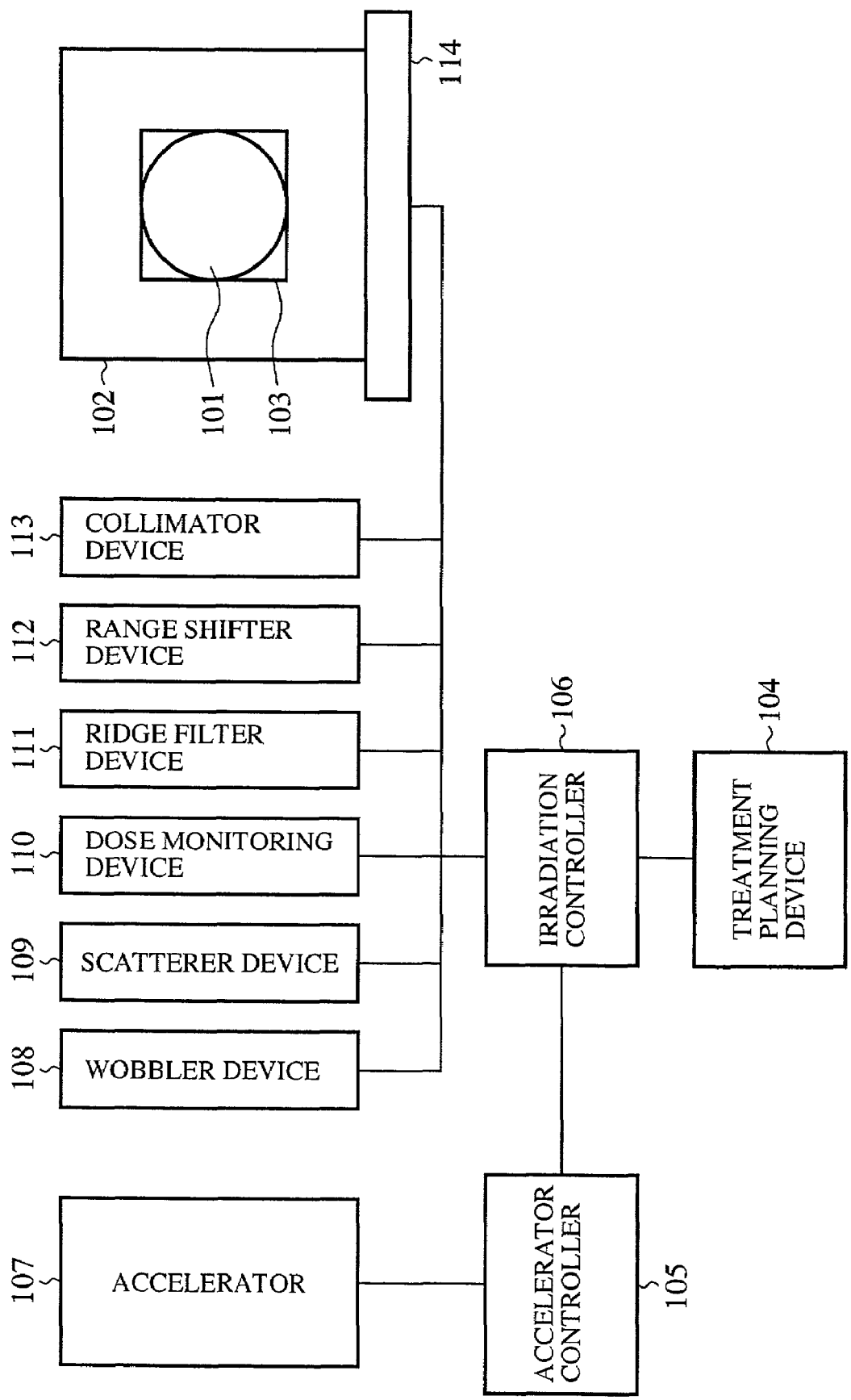

RADIATION TREATMENT PLAN MAKING SYSTEM AND METHOD

BACKGROUND OF THE INVENTION

1. Field of the Invention

The present invention relates to a radiation treatment system designed to treat a tumor or the like in the body or the body surface of a patient by irradiating the tumor with particle beams such as a proton beam, a carbon beam or the like. More particularly, the invention relates to a radiation treatment system and a method thereof, capable of maintaining flatness, which indicates the degree of uniform radiation beam irradiation in an area to be exposed to radiation, by dividing the area to be exposed to radiation including its peripheral area into a plurality of areas, and then performing the simulation of radiation exposure according to the shape of each area, and improving the efficiency of radiation utilization.

2. Description of the Related Art

The radiotherapy is a method of treatment employed to reduce or even remove a tumor by intensively applying radiation to the tumor generated in the body of a patient. When such a radiation exposure treatment is carried out, the area to be exposed to radiation including the tumor to be treated must be uniformly irradiated with a proper dose of radiation. On the other hand, radiation applied to a healthy organization around the tumor outside the area to be exposed to radiation must be suppressed as much as possible.

Now, description will be made as to the radiation treatment system which uses particle beams among the radiations used for the above-described radiotherapy. Here, to briefly explain the principle of the radiation treatment system, consideration is given to a case where an area to be treated is a ball having a radius r, a patient is regarded as a cube having one side set equal to 4r, and the center of the ball as the area to be treated is located at the center of the cube.

FIG. 9 illustrates the configuration of a radiation treatment system using such particle beams available in the related art. In the drawing, a reference numeral 101 denotes a region to be treated by radiotherapy (hereinafter may be referred to just as treatment region), in which a tumor or the like to be subjected to radiation exposure is present. This region is assumed to be a ball having a radius r, and the center of the ball is located at a cubic center of a patient 102 assumed as a cube having one side set equal to 4r. A reference numeral 102 denotes a patient fixed to a treatment couch 114, and irradiated with particle beams; 103 a radiation exposure region defined in a three-dimensional area which includes a treatment region 101; 104 a treatment planning device designed to perform treatment simulation for forming a radiation exposure region 103 according to the state of the diseased part of the patient 102 to be treated, and setting parameters for the direction of irradiation, the position of irradiation, and so on; 105 an accelerator controller for controlling the operation of an accelerator 107, specifically designed to adjust a radiation beam to appropriate strength according to the acceleration condition in the treatment simulation performed by the treatment planning device 104; and 106 an irradiation controller designed to control a wobbler device 108, a scatterer device 109, a dose monitoring device 110, a ridge filter device 111, a range shifter device 112, and a collimator device 113 respectively according to a set condition in the treatment simulation, thereby controlling the irradiation direction, position, and so on, of the radiation beam.

A reference numeral 107 denotes an accelerator for offering energy to the radiation beam, a cyclotron, a synchrotron, or the like for accelerating the radiation beam containing charged particles by the acceleration electric field of high frequency being used therefor; 108 a wobbler device used to expand the radiation beam corresponding to the radiation exposure region 103, composed of a deflection electromagnet, and adapted to move the radiation beam so as to draw a circular orbit on the radiation exposure region 103 by applying a sinewave current having a phase different by 90° to this deflection electromagnet; 109 a scatterer device composed of a scatterer for scattering the radiation beam, and used to expand the radiation beam with the wobbler device 108 corresponding to the radiation exposure region 103; 110 a dose monitoring device for monitoring the dose of the radiation beam applied to the radiation exposure region 103, designed to output each dose of the radiation beam monitored to the irradiation controller 106; 111 a ridge filter device used for modulating the range of the radiation beam, generally made of brass or the like having a proper shape on the surface, and designed to adjust the expanse in the advancing direction of the radiation beam; 112 a range shifter device for adjusting a reaching distance in the advancing direction of the radiation beam according to the set condition in the treatment simulation; 113 a collimator device for adjusting the passage aperture of the radiation beam corresponding to the radiation exposure region 103; and 114 a treatment couch for laying the patient 102 thereon.

Next, the operation of the system as configured above will now be described as below.

First, before a particle beams treatment is carried out, the image data of a diseased part obtained by photographing the diseased part (equivalent to the treatment region 101) of the patient 102 with an X-ray CT not-shown is output to the treatment planning device 104. Based on the state of the diseased part analyzed from the input image data thereof, the treatment planning device 104 decides a radiation exposure region 103 by adding an area or the like as a margin to the treatment region 101, and then performs treatment simulation for setting parameters for the direction of irradiation, the position of irradiation, and so on.

In this case, in the radiation treatment system available in the related art, when the treatment region 101 is formed to be a ball having a radius r, a radiation exposure region 103 becomes a circle having a radius r. Then, the ridge filter device 111 having a width of 2r of SOBP (spread out Bragg peak) in the advancing direction of the radiation beam is used. Moreover, in the accelerator 107, the radiation beam is accelerated by acceleration energy that causes the reaching distance of particle beams in the body of the patient 102 to be 3r. Then, the treatment simulation is executed by the wobbling device 108 and the scatterer device 109 such that the radiation beam is uniformly applied in the radiation exposure region 103 (flattening).

Besides the foregoing, in order to accurately irradiate the radiation exposure region 103 with the radiation beam, there are cases where a collimator dedicated to the patient having a cylindrical radiation beam passage aperture is used, and the collimator device 113 having general applicability is used. FIG. 9 shows the example of using the collimator device 113.

Now, the treatment simulation will be described in detail. The treatment planning device 104 calculates a parameter to be set for the collimator device 113, assuming that the collimator is usually circumscribed on the circular radiation exposure region 103 having a radius r. Then, corresponding to the radiation exposure region 103, the treatment planning device 104 selects operation conditions for the wobbler device 108 and the scatterer device 109 for expanding the radiation beam. In addition, the ridge filter for causing the expanse in the advancing direction of the radiation beam to be 2r is selected.

In this case, if the reaching distance of the radiation beam is not exactly 3r in the body of the patient 102, then the treatment planning device 104 selects an operation condition for the accelerator 107 for offering radiation beam energy to realize a reaching distance of 3r or more. Subsequently, a difference in the reaching distance equivalent to the acceleration energy offered by the accelerator 107 and the reaching distance 3r of the radiation beam in the body of the patient 102 is adjusted by the range shifter device 112. The treatment planning device 104 decides an irradiation condition of the radiation beam to coincide with the deepest part in the radiation exposure region 103, and also decides the irradiation dose of particle beams at this time.

Checking is made as to the appropriateness of the dose distribution decided by the treatment planning device 104. If appropriate, then the treatment planning device 104 outputs the set parameter of the radiation treatment system which has been obtained in the treatment simulation, to the accelerator controller 105 and the irradiation controller 106. Upon having received the treatment parameter, the accelerator controller 105 and the irradiation controller 106 set the above-mentioned treatment parameter in each of the accelerator 107, the wobbler device 108, the scatterer device 109, the dose monitoring device 110, the ridge filter device 111, the range shifter device 112, and the collimator device 113.

Then, the patient 101 is laid on the treatment couch 114 and fixed, and the radiation exposure region 103 is aligned with the position of irradiation, and irradiated with particle beams. When the dose monitoring device 110 determines that the prescribed dose of radiation beam has been applied, the irradiation with the radiation beam is stopped, completing one treatment.

Next, description will be made as to a general method for performing flattening to uniformly irradiate the radiation exposure region 103 with the radiation beam, used in the particle-beams treatment. Hereinafter, the irradiation of the radiation exposure region 103 uniformly with the radiation beam is simply referred to as the flattening of a radiation field for the easiness of explanation.

In general, for the flattening of the radiation field, there are available a double scatterer system using a double scatterer, and a wobbler system using the wobbler device. These systems are both designed to form a circular radiation field (circular radiation exposure region 103).

More specifically, the double scatterer system increases the level of scattering the radiation beam by using two kinds of scatterers arranged away from each other in the axial direction of the radiation beam, and flattens the radiation field by performing scattering in such a way as to increase the efficiency of using the radiation beam. There is a close relation between the size of the radiation field (radiation exposure region 103), and the scattering conditions of the two kinds of scatterers and the shapes thereof. The efficiency of using particle beams in the double scatterer system is generally about 30%. The efficiency of using particle-beams is equivalent to the ratio of a dose of radiation applied in the radiation field with respect to all doses of radiation including a dose of radiation applied outside the radiation field for the flattening of the radiation field.

The wobbler system rotates the radiation beam by the wobbler device for generating a rotating magnetic field, scatters the radiation beam by the scatterer to expand a beam diameter, and then forms a radiation field having prescribed flatness (degree of uniformity when the radiation exposure region 103 is irradiated with the radiation beam, given by a difference in the reaching amounts of the radiation beams applied to the radiation exposure region 103) when the radiation beam makes one rotation. In this wobbler system, when the radiation field is enlarged, the rotational radius of the radiation beam is increased, and the thickness of the scatterer for expanding the radiation beam is increased.

There is a relation given by an equation below among the size ($r_{max}$) of the radiation field, the rotational diameter ($R_O$) of the radiation beam, and the expanse ($\sigma_a$) of the radiation beam, when the flatness of the radiation field is ±2%. In this case, the radiation field is formed based on the characteristic of the radiation beam supplied from the accelerator according to a prescribed relational equation. In the wobbler system, since particle beams in the area of 84% inside the rotational radius of the radiation beam is used, the efficiency of using particle beams becomes about 30%.

$$R_O : \sigma_a : r_{max} = 1.00 : 0.90 : 0.84$$

Here, $r_{max}$ in the above-mentioned relational equation becomes small when the flatness is further increased to reach ±1%, and the efficiency of using the particle beams is lowered.

The radiation treatment system of the related art is constructed in the foregoing manner, and the treatment simulation is performed for the circular radiation exposure region 103 formed by the double scatterer system or the wobbler system to decide parameters to be set for the respective devices. Consequently, the efficiency of using particle beams has been low.

To explain the foregoing problem more specifically, an actual radiation exposure region 103 is not always a circular radiation field. Thus, when the radiation field is subjected to flattening by the double scatterer system or the wobbler system, the proportion of particle beams applied outside the radiation exposure region 103 is increased, bringing about a reduction in the efficiency of using particle beams. For example, the efficiency of particle beams in the foregoing wobbler system was theoretically 30%. Actually, however, the efficiency is lower than this value, and if the radiation exposure region 103 occupies only ½ of the circular radiation field, then the efficiency of using particle beams is lowered to 15%.

SUMMARY OF THE INVENTION

The present invention was made to solve the foregoing problems. Objects of the invention are to provide a radiation treatment system and a radiation treatment method, capable of maintaining flatness, which is a degree of uniformly irradiating a region to be exposed to radiation with a radiation beam, and increasing the efficiency of using particle beams, by dividing a radiation exposure region including a region to be irradiated with particle beams and a peripheral region thereof into a plurality of unit radiation exposure regions, and then executing radiation treatment simulation according to the shape of each divided region.

In accordance with an aspect of the invention, there is provided a radiation treatment system, comprising: simulation means for executing radiation treatment simulation for dividing a radiation exposure region and a peripheral region thereof to be irradiated with particle beams into a plurality of unit radiation exposure regions, and then applying particle beams according to a shape of each divided unit radiation exposure region; and radiation treatment planning means for obtaining a radiation treatment condition for causing flatness, which is a degree of uniformly irradiating the radiation exposure region with a proper dose of particle beams, to be in a desired range, and a dose of particle beams applied to the unit radiation exposure region of the peripheral region to be minimized, in the case where the simulation means executes the radiation treatment simulation, and then making a radiation treatment plan reflecting the radiation treatment condition.

According to the radiation treatment system of the invention, the simulation means divides the radiation exposure region and the peripheral region thereof into unit radiation exposure regions of grid forms.

According to the radiation treatment system of the invention, the simulation means divides the radiation exposure region and the peripheral region thereof into belt-like unit radiation exposure regions.

According to the radiation treatment system of the invention, the simulation means divides the radiation exposure region and the peripheral region thereof into concentric circular unit radiation exposure regions.

According to the radiation treatment system of the invention, when the unit radiation exposure region is located in a boundary of the radiation exposure region, the radiation treatment planning means determines a degree of contribution made by a dose of particle beams applied to the unit radiation exposure region located in the boundary to the radiation exposure region, according to a dose of particle beams applied to the unit radiation exposure region of the peripheral region.

In accordance with another aspect of the invention, there is provided a radiation treatment method, comprising: a simulation step for dividing a radiation exposure region and a peripheral region thereof to be irradiated with particle beams into a plurality of unit radiation exposure regions, and then executing radiation treatment simulation according to a shape of each divided unit radiation exposure region; a radiation treatment planning step for obtaining a radiation treatment condition for causing flatness, which is a degree of uniformly irradiating the radiation exposure region with a proper dose of particle beams, to be in a desired range in the case where the simulation step is executed and a dose of particle beams applied to the unit radiation exposure region of the peripheral region to be minimized, and then making a radiation treatment plan reflecting the radiation treatment condition; and a radiation exposure step for applying particle beams to the radiation exposure region and the peripheral region thereof to be irradiated according to the radiation treatment plan made in the radiation treatment planing step.

According to the radiation treatment method of the invention, in the simulation step, the radiation exposure region and the peripheral region thereof are divided into unit radiation exposure regions of grid forms.

According to the radiation treatment method of the invention, in the simulation step, the radiation exposure region and the peripheral region thereof are divided into belt-like unit radiation exposure regions.

According to the radiation treatment method of the invention, in the simulation step, the radiation exposure region and the peripheral region thereof are divided into concentric circular unit radiation exposure regions.

According to the radiation treatment method of the invention, in the radiation treatment planning step, when the unit radiation exposure region is located in a boundary of the radiation exposure region, determination is made as to a degree of contribution made by a dose of particle beams applied to the unit radiation exposure region located in the boundary to the radiation exposure region, according to a dose of particle beams applied to the unit radiation exposure region of the peripheral region.

BRIEF DESCRIPTION OF THE DRAWINGS

FIG. 9 is a view showing a configuration of a radiation treatment system of the related art.

DETAILED DESCRIPTION OF THE PREFERRED EMBODIMENTS

Next, the preferred embodiments of the present invention will be described.

First Embodiment

Figure 1:
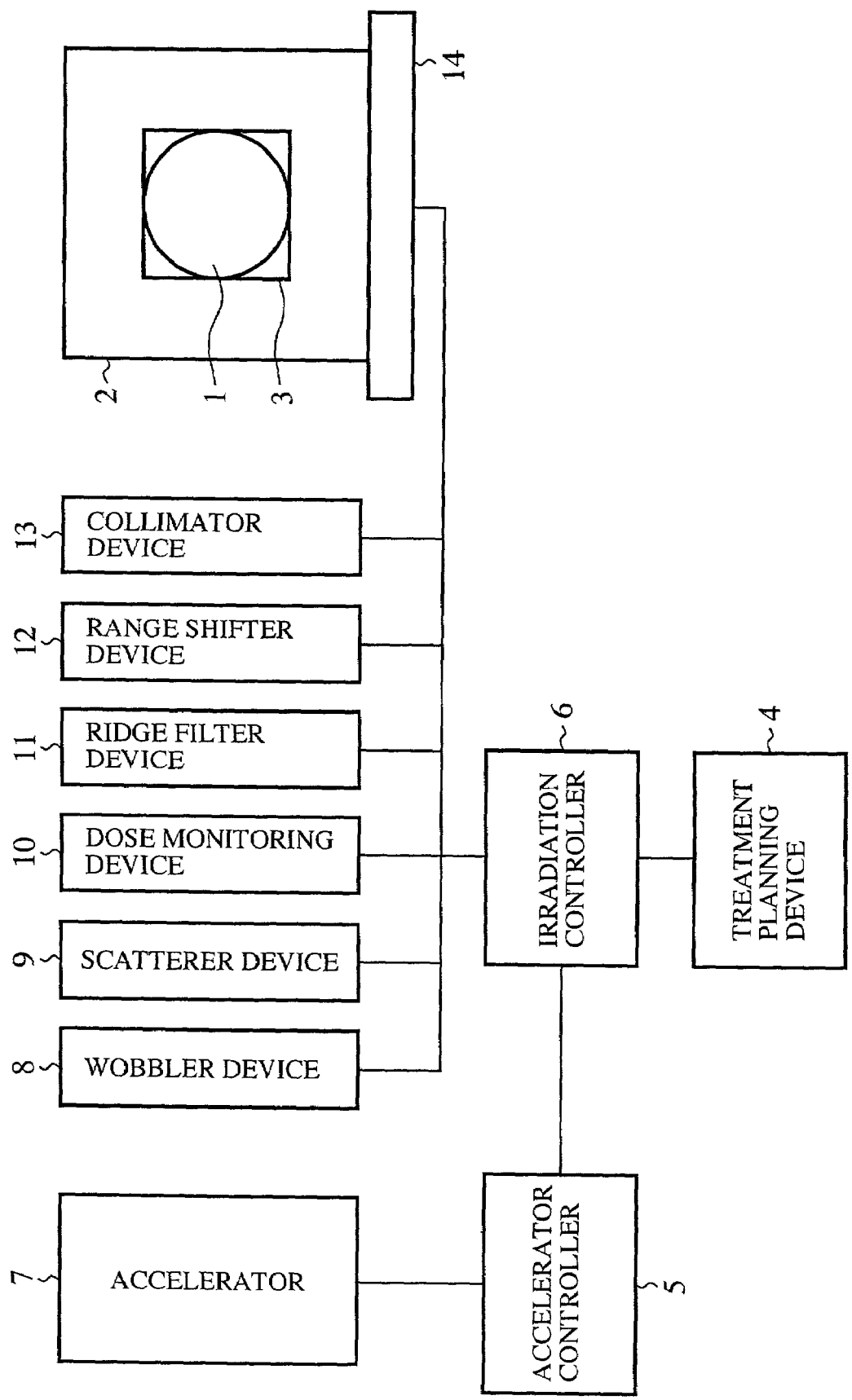
FIG. 1 is a view showing a configuration of a radiation treatment system according to a first embodiment of the present invention.

FIG. 1 illustrates the configuration of a radiation treatment system according to the first embodiment of the invention. In the drawing, a reference numeral 1 denotes a treatment region, in which a tumor or the like is present to be subjected to radiation treatment, which treatment region being assumed to be a ball having a radius r, and the center thereof being located at a cubic center of a patient 2 assumed to be a cube having one side set to 4r; 2 a patient fixed to a treatment couch 14, and subjected to radiation exposure; 3 a radiation exposure region to be irradiated with particle beams, defined by a three-dimensional region including the treatment region 1; and 4 a treatment planning device (simulation means and irradiation planning means), adapted to form a radiation exposure region 3 according to the state of the diseased part of the patient 2, divide the thus formed radiation exposure region 3 and the peripheral region thereof in a grid form, and set a control parameter (radiation treatment condition) for each device to apply particle beams according to a grip point (unit irradiation region) in an accelerator controller 5 and an irradiation controller 6. Besides the foregoing, the treatment planning device 4 obtains a control parameter for each device to cause the flatness of the radiation exposure region 3 to be in a desired range, and the number of grid points irradiated with particle beams in the peripheral region to be minimum, when the accelerator controller 5 and the irradiation controller 6 execute treatment simulation (radiation treatment simulation) according to the above-described set control parameter, and then makes a radiation treatment plan reflecting this.

A reference numeral 5 denotes an accelerator controller (simulation means) for controlling the operation of a controller 7, adapted to adjust radiation beam strength in the treatment simulation according to the control parameter input from the treatment planning device 4; 6 an irradiation controller (simulation means), adapted to execute the treatment simulation by controlling each of a wobbler device 8, a scatterer device 9, a dose monitoring device 10, a ridge filter device 11, a range shifter device 12, and a collimator device 13 according to a set condition of the control parameter input from the treatment planning device 4; 7 an accelerator for offering energy to the radiation beam, for which a cyclotron or a synchrotron for accelerating the radiation beam composed of charged particles by the acceleration electric field of high frequency as in the case described above in the related art; 8 a wobbler device for irradiating the grid point with the radiation beam by providing a prescribed angle of deflection to particle beams with a deflection electromagnet, an energizing current for which is controlled by irradiation controller 6; and 9 a scatterer device for receiving the entry of the radiation beam output from the wobbler device 8, and providing a prescribed shape to the radiation beam, composed of a scatterer for scattering the radiation beam.

A reference numeral 10 denotes a dose monitoring device for monitoring a dose of the radiation beam applied to the radiation exposure region 3, adapted to output each monitored dose of the radiation beam to the irradiation controller 6; 11 a ridge filter device used for modulating the range of the radiation beam, made of brass or the like having a proper shape formed in the surface as in the case described above in the related art, and designed to adjust the expanse in the advancing direction of the radiation beam; 12 a range shifter device for adjusting the reaching distance of the radiation beam in its advancing direction according to the set condition in the treatment simulation; 13 a collimator device for adjusting the passage aperture of the radiation beam corresponding to the radiation exposure region 3; and 14 a treatment couch for laying the patient 2. Now, description will be made as to the radiation treatment system using particle beams according to the first embodiment.

Figure 2:
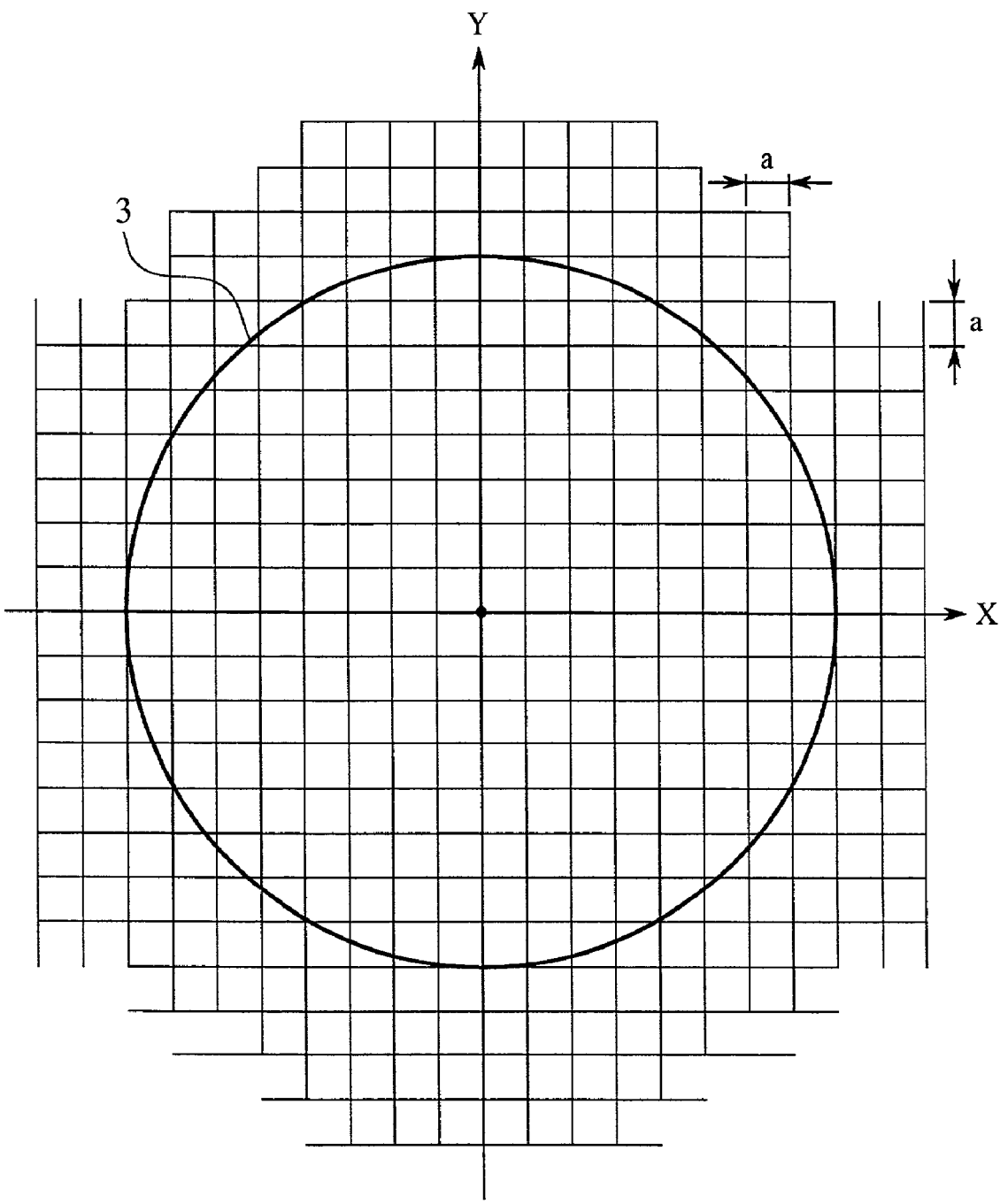
FIG. 2 is a view showing an example of division into a radiation exposure region and a peripheral region thereof according to the first embodiment.

FIG. 2 shows the example of division into a radiation exposure region and a peripheral region thereof according to the first embodiment. In FIG. 2, the radiation exposure region 3 is divided into a plurality of squares having one side a in each of X and Y axes, with a treatment center equivalent to the center of the radiation exposure region 3 as an original point. In addition, the peripheral region outside the radiation exposure region 3 is similarly divided. The radiation treatment system of the first embodiment applies particle beams to the intersection (grid point) of longitudinal and horizontal lines constituting a boundary line of each square having one side a in FIG. 2.

Description will be made as to a flattening condition for the radiation exposure region 3 (referred to as the flattening of a radiation field, hereinafter), before the explanation of the operation of the radiation treatment system of the first embodiment. Generally, the beam of particle beams can be approximated to Gaussian distribution. In the first embodiment, the radiation beam is processed as one subjected to Gaussian distribution.

First, the flattening condition of the radiation field when particle beams having two-dimensional Gaussian distribution are used is obtained as follows. When an isotropic beam shape of two-dimensional Gaussian distribution is equivalent to standard deviation $\sigma_{xy}$, the beam shape (beam size) of particle beams having two-dimensional Gaussian distribution is given by an equation (1) described below. In addition, when the radiation beam is moved in a plane including regions divided at equal intervals a (stepsize $\Delta X$ and $\Delta Y$), and the respective points are irradiated by equal doses, a dose distribution can be calculated by an equation (2) decried below:

$$d(x_i, y_j, x, y) = \frac{1}{2\pi\sigma_{xy}^2} e^{-\frac{(x-x_i)^2+(y-y_j)^2}{2\sigma_{xy}^2}} \tag{1}$$

$$D(x, y) = \sum_{i,j} d(x, y, x_i, y_j) \tag{2}$$

Here, $x_i$ and $y_j$ are given by an equation (3) below:

$$x_i = i \times \Delta x, \ y_j = j \times \Delta y \tag{3}$$

In this case, i, j=±1, ±2, and is ±3, and ±4 . . .

Figure 3:
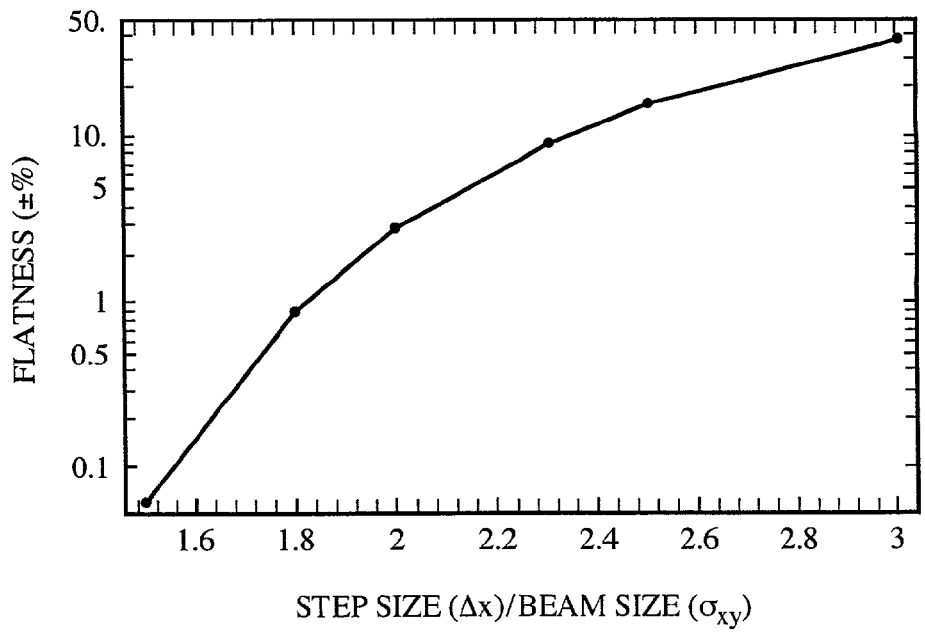
FIG. 3 is a graph showing a relation between a value of a step size of a radiation beam standardized by an isotropic radiation beam shape (standard deviation $\sigma_{xy}$) and flatness of a radiation field.

FIG. 3 is a graph showing a relation between a value of a stepsize of a radiation beam standardized by an isotropic beam shape of particle beams (standard deviation $\sigma_{xy}$) and the flatness of the radiation field. As shown in the same graph, assuming the relation of $\Delta x = \Delta y$, from the foregoing relational equation, the flatness of the radiation field is gently and monotonously increased with respect to values of the stepsizes $\Delta X$, and $\Delta Y$ of the radiation beam standardized by the beam shape (standard deviation $\sigma_{xy}$). Here, for example, assuming that the flatness of the radiation field is ±1%, then it can be understood that a stepsize is to be set equal to the beam shape (standard deviation $\sigma_{xy}$) by 1.8 times. This means that if a division interval a is set to an optionally-given beam shape by 1.8 times, the flatness of the radiation field in a horizontal direction becomes ±1%. Accordingly, if a stepsize in the horizontal direction has been decided, then the beam shape only needs to be set to a/1.8. Assuming that flatness is ±2%, as can be understood from FIG. 3, a stepsize only needs to be set equal to the beam size by about 1.9 times.

On the other hand, to set the flatness of the radiation field within the range of ±1% as described above, a stepsize of particle beams only needs to be set equal to the beam size (standard deviation $\sigma_{xy}$) by 1.8 times or less than 1.8 times. This means that when particle beams are applied in a grid form, a contribution is made from particle beams applied from the most adjacent grid point away by $1.8\sigma_{xy}$, but since a next most adjacent grid point away by $1.8\sigma_{xy}$ is totally separated by $3.6\sigma_{xy}$, the contribution of particle beams can be almost ignored. In other words, at a grid point outside the end of the radiation field (peripheral region of the radiation exposure region 3), there is no need of irradiating the grid point away by $5.4\sigma_{xy}$ with particle beams in terms of safety. Therefore, the flatness of the radiation field can be sufficiently secured by performing radiation exposure from the end of the radiation field (boundary of the radiation exposure region 3) to the grid point away by $3.6\sigma_{xy}$.

As for the condition that the desired flatness of the radiation field like that described above is obtained, and the grid point in the peripheral region of the radiation exposure region 3 minimized (that is, dose of particle beams applied to the peripheral region is minimized), a specific control parameter is calculated by the treatment planning device 4 during the execution of the treatment simulation.

Next, the operation of the system as configured above will now be described as below.

First, before the execution of particle-beams treatment, the diseased part (equivalent to the treatment region 1) of the patient 2 is photographed by an X-ray CT, not shown, and then the obtained image data of the diseased part is output to the treatment planning device 4. Based on the state of the diseased part analyzed from the input image data of the diseased part, the treatment planning device 4 decides a radiation exposure region 3 by adding a region or the like as a margin to the treatment region 1. In this case, in the treatment simulation, in which a region to be irradiated with particle beams is formed at the treatment planning device 4 according to the first embodiment, the radiation exposure region 3 and the peripheral region thereof are divided in grid forms as shown in FIG. 2, and all the grid points thereof (unit radiation exposure regions) are irradiated with equal doses of particle beams.

The treatment planning device 4 calculates a control parameter for irradiating each of the above grid points with particle beams, and outputs the control parameter to the accelerator controller 5 and the irradiation controller 6. According to the control parameter from the treatment planning device 4, the irradiation controller 6 sets a leaf control parameter for the collimator device 13 to be circumscribed on the radiation exposure region 3 which is assumed to be a circle having a radius r. In addition, the irradiation controller 6 controls the operations of the wobbler device 8, the scatterer device 9, the dose monitoring device 10, the ridge filter device 11, and the range shifter device 12. Then, the accelerator controller 5 associatively controls the accelerator 7. Accordingly, particle beams having a beam size decided by the interval length of the grid points shown in FIG. 3 are generated, and treatment simulation is executed (simulation step). Here, to irradiate the grid points with particle beams, the energizing current of the wobbler device 8 is controlled by the irradiation controller 6. Then, the irradiation can be executed by providing a prescribed angle of deflection to the particle beams.

In the treatment simulation executed in the foregoing manner, determination is made as to up to which of the grid points located outside the end of the radiation exposure region 3 is to be irradiated with particle beams by the treatment planning device 4, in order to obtain desired flatness inside the radiation exposure region 3.

In addition, in the foregoing case, no particle beams need to be applied to a portion away by 3 grid points or more from the end of the radiation exposure region 3. Thus, a coordinate of the grid point to be irradiated with particle beams can be calculated by the treatment simulation. Now, the reason for the unnecessity of applying particle beams to the portion away by 3 grid points or more from the end of the radiation exposure region 3 will be described. Strength is reduced to $0.368(1/e; e=2.71828\ldots)$ of strength of the center portion, when separation is made by only a distance equivalent to the standard deviation $\sigma$ in two-dimensional Gaussian distribution, from the center of the radiation beam (beam axis). Because strength is generally reduced to less than 0.01 of strength of the center portion when separated by $3\sigma$, particles entering the radiation exposure region 3 from the grid point away by $3\sigma$ from the center portion gives almost no influence on the flatness (0.01) of the radiation field of 1%, which is considered to be less than 0.01. Accordingly, in the first embodiment, contribution made from the grid point away from 3 grid points or more from the end of the radiation exposure region 3 to the inside of the same is ignored.

In the treatment simulation executed in the foregoing manner, according to a relation like that shown in FIG. 3, the treatment planning device 4 calculates a control parameter for providing a radiation treatment condition, by which a desired flatness of a radiation field is set, and a dose of particle beams applied to the outside of the radiation exposure region 3 is minimized. Then, by using the dose monitoring device 10, determination is made as to whether the dose distribution of particle beams applied by the treatment planning device 4 according to the control parameter is appropriate or not. If the appropriate dose distribution is determined, then, the treatment planning device 4 makes a radiation treatment plan reflecting the control parameter for the grid point to be irradiated with particle beams (radiation treatment planning step).

The control parameter in the radiation treatment plan is output from the treatment planning device 4 to the accelerator controller 5 and the irradiation controller 6. The accelerator controller 5 and the irradiation controller 6 set the same control parameter as that of the treatment simulation input from the treatment planning device 4 in the accelerator 7, the wobbler device 8, the scatterer device 9, the dose monitoring device 10, the ridge filter device 11, and the range shifter device 12. In addition, open-degree data corresponding to the radiation exposure region 3 is calculated, and set in the collimator device 13.

Then, the patient 2 is laid on the treatment couch 14 and fixed, and the radiation exposure region 3 is aligned with a position for radiation exposure. The irradiation controller 6 controls the wobbler device 8 to set particle beams in a position corresponding to the grid point to be irradiated with particle beams, when the radiation exposure region 3 is subjected to radiation exposure. In addition, the irradiation controller 6 sets a scatterer for providing a prescribed beam shape to the scatterer device 9, and then sets a dose of particle beams to be applied in the dose monitoring device 10 according to the radiation treatment plan.

After the control parameter has been set in the foregoing manner, the irradiation of each grid point with particle beams is started. When a dose monitored by the dose monitoring device 10 reaches a prescribed value, then the irradiation controller 6 stops the radiation beam and performs control in such a way as to move particle beams to a next grid point. Then, the same dose of particle beams is set on the dose monitoring device 10, and the radiation exposure is carried on (radiation exposure step). After the foregoing operation has been carried out for all the grid points to be irradiated with particle beams, one radiation treatment is completed.

According to the first embodiment, if no particle beams are applied to the peripheral region located within 3 grid points from the end (boundary) of the radiation exposure region 3 to flatten the radiation field, flatness inside the radiation exposure region 3 cannot be secured. Consequently, a part of the particle beams applied to the peripheral region located within 2 grid points from the end (boundary) of the radiation exposure region 3 is wasted.

In other words, assuming that the radiation exposure region 3 is a circle having a radius r and its diameter 2r is equivalent to the number n of grid points, the number of grid points necessary for flattening the radiation field can be approximated by a circle area having a diameter (n+4) obtained by adding an amount equivalent to two grid points from the end of the radiation exposure region 3. The efficiency of using particle beams is given by the ratio of the number of grid points in the radiation exposure region 3 and the number of grid points in a region where the 2 grid points of the peripheral region are added to the radiation exposure region 3. Accordingly, the efficiency is given by $(n/(n+4))^2$ considering that particle beams outside the radiation exposure region 3 are all wasted. Therefore, it can be understood that to secure 30% efficiency of using particle beams, n must be set equal to 5 or higher.

In addition, the radiation exposure region 3 was a circle in the foregoing. Generally, however, the radiation exposure region 3 is not a circular radiation field. Thus, the efficiency of using particle beams was lower than the theoretical value of 30% in the method of the related art. For example, if the radiation exposure region 3 occupies only ½ of the circular radiation field, then the efficiency of using particle beams is lowered to 15%. On the other hand, according to the first embodiment, particle beams are applied only to the necessary grid points outside the actual radiation exposure region 3. Thus, even if the radiation exposure region 3 is divided into less than 5 in a grid form in the directions of X and Y axes, the actual efficiency of using particle beams can be increased.

In addition, in the foregoing description, it is shown that the radiation exposure region 3 and the peripheral region thereof are divided from the treatment center in the directions of X and Y axes as shown in FIG. 2. However, a similar advantage can be obtained even by setting grid points in an orthogonal directions with a given point used as a reference.

Further, the division was made into squares having one side a in FIG. 2. However, another division is possible.

Figure 4:
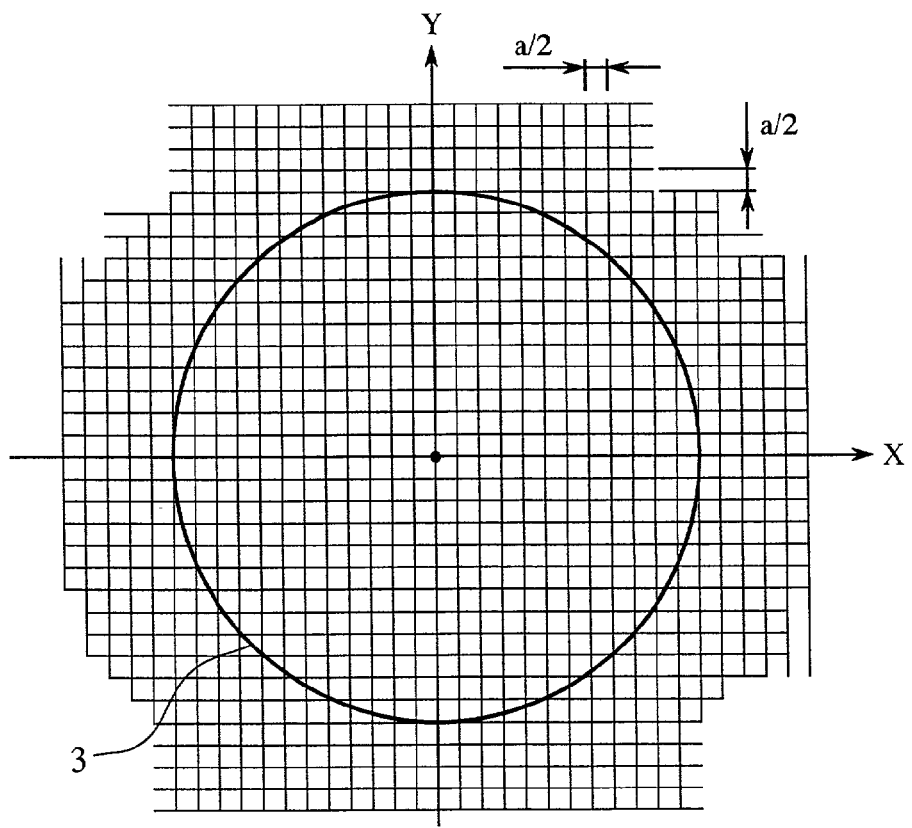
FIG. 4 is a view showing another example of division into a radiation exposure region and a peripheral region thereof according to the first embodiment.

FIG. 4 shows another example of division for the radiation exposure region and the peripheral region thereof according to the first embodiment. As shown, the radiation exposure region 3 and the peripheral region thereof may be divided into squares having one side of a/2, stepsizes in the directions of X and Y axes may be set to a, and radiation exposure may be carried out by shifting a/2 when a next line is irradiated. In this way, the flattening condition of the radiation field can be obtained in the treatment simulation as in the case of the first embodiment. Thus, a similar advantage can be achieved.

In addition, the radiation exposure region 3 and the peripheral region thereof were divided into the squares. However, even if theses regions are divided into given identical shapes r (diamond, or rectangle) other than squares, a dose of particle beams applied to each grid point for flattening the radiation exposure region 3 is reverse-calculated with the dose of particle beams applied to each grid point set as a parameter. In this case, if there is a solution to the calculation, then a similar advantage can be obtained.

In addition, the analysis was made assuming that the beam shape (standard deviation $\sigma_{xy}$) isotropic as shown in FIG. 3. However, even the beam shape is not isotropic, simulation for optimizing a stepsize according to the beam shape can be carried out. Thus, a similar advantage can be obtained.

In addition, the case where the radiation exposure region 3 was a circle was described. However, even if the radiation exposure region 3 takes a given shape, a similar advantage can be obtained by carrying out simulation for applying particle beams to a region away by 2 grid points from the end of the radiation exposure region 3.

Further, the case where the flatness of the radiation exposure region 3 was ±1% was described. However, even if flatness is set to a given value, a similar advantage can be obtained.

As apparent from FIG. 3, generally, the stepsize is smaller as the flatness of the radiation exposure region is improved. The stepsize is larger as the flatness of the radiation exposure region 3 is degraded. The dose of particle beams applied to the grid point located outside from the end of the radiation exposure region 3 is increased by increasing the flatness of the radiation exposure region 3. However, the dose of particle beams applied to the grid point located inside the radiation exposure region 3 is also increased. On the other hand, if the flatness is lowered, the dose of particle beams applied to the grid point located outside from the end of the radiation exposure region 3 is reduced. However, the dose of particle beams applied to the grid point located inside the radiation exposure region 3 is also reduced.

Considering the above relation, it can be understood that the efficiency of using particle beams is not so dependent on the simulated flatness if the range of flatness to be used for radiation exposure treatment is about 0.5–5%, and the standard deviation $\sigma_{xy}$ of the beam shape is about 1.7–2.1.

In addition, in the example described above with reference to FIG. 2, there was no mention of the order of irradiating the grid points with particle beams. However, since the irradiation order of the grid points is not so important for the formation of the radiation exposure region 3, a similar advantage can be obtained even in the order of the grid points facilitating the control of the wobbler device 8 or in the order facilitating control data creation.

Moreover, if the contribution of the dose of particle beams in each grid point is the same, a similar advantage can be provided even if irradiation is carried out not just once but by a plurality of times.

In addition, the example of division made such that the grid point coincided with the end of the diameter part of the circular radiation exposure region 3 was shown. However, even if the grid point does not coincide with the end of the diameter part of the radiation exposure region 3, a similar advantage can be obtained by simulating the dose of particle beams applied to the grid point located outside the radiation exposure region 3 and including the grid point contributing to the radiation exposure region 3.

Further, description was made of the example of irradiating the grid points with the similar doses of particle beams having similar beam shapes when the grid points were regularly disposed. However, though calculation becomes a complex equation, a similar advantage can be obtained if there is solution to a reverse-problem for flattening the inside of the radiation exposure region 3, even when particle beams having different beam shapes are applied to irregularly disposed grid points.

In addition, assuming that the exposure position to be irradiated with particle beams changes timewise, if there is reproducibility or regularity in such a change, for the actual exposure position of each grid point, it is also possible to calculate a dose of particle beams applied to each grid point by the method described above. On the other hand, if there is no reproducibility or regularity in the change, then, a flattening condition for the radiation exposure region 3 can be obtained by including the width of the change in the beam shape of the applied particle beams.

As described above, according to the first embodiment, the radiation exposure region 3 and the peripheral region thereof to be irradiated with particle beams are divided in the grid forms, and the treatment simulation for applying particle beams according to each divided grid point is carried out. During the treatment simulation, the radiation treatment condition for causing the flatness of the radiation exposure region 3 to be in a desired range, and the dose of particle beams applied to the grid point of the peripheral region to be minimized is obtained, the radiation treatment plan is made reflecting this radiation treatment condition and, based on this treatment plan, the radiation exposure region 3 and the peripheral region to be irradiated are subjected to radiation exposure. Thus, since the unit radiation exposure regions obtained by dividing the radiation exposure region 3 and the peripheral region thereof into pluralities of regions are used, it is possible to accurately decide a radiation exposure region for providing desired flatness, and to increase the efficiency of using particle beams compared with the case of the related art. Moreover, since particle beams are applied to the minimum grid points in the peripheral region for providing desired flatness, it is possible to suppress the generation of superfluous particle beams.

Second Embodiment

The radiation treatment system of the second embodiment is basically similar in configuration to that of the first embodiment. Thus, description will be made of portions different from those of the first embodiment.

First, the treatment planning device 4 (simulation means and irradiation planning means) of the second embodiment forms a radiation exposure region 3 according to the state of the diseased part of the patient 2 to be treated as in the case of the first embodiment, divides the radiation exposure region 3 and the peripheral region thereof into belt forms, and then sets a control parameter (radiation treatment condition) of each device for applying particle beams according to the center Line of the belt form (unit radiation exposure region) in the accelerator controller 5 and the irradiation controller 6. The accelerator controller 5 and the irradiation controller 6 execute treatment simulation for applying particle beams according to the center Line of the belt regions divided based on the control parameter. In the treatment simulation, the treatment planning device 4 obtains a control parameter of each device for causing the flatness of the radiation exposure region 3 to be in a desired range and the dose of particle beams to be applied to the peripheral region to be minimized, and then makes a radiation treatment plan reflecting the control parameter.

Also, in the second embodiment, as in the case of the first embodiment, a treatment region 1 is assumed to be a ball having a radius r, and the center thereof is located at the cubit center of the patient 2 assumed to be a cube having one side 4r.

Figure 5:
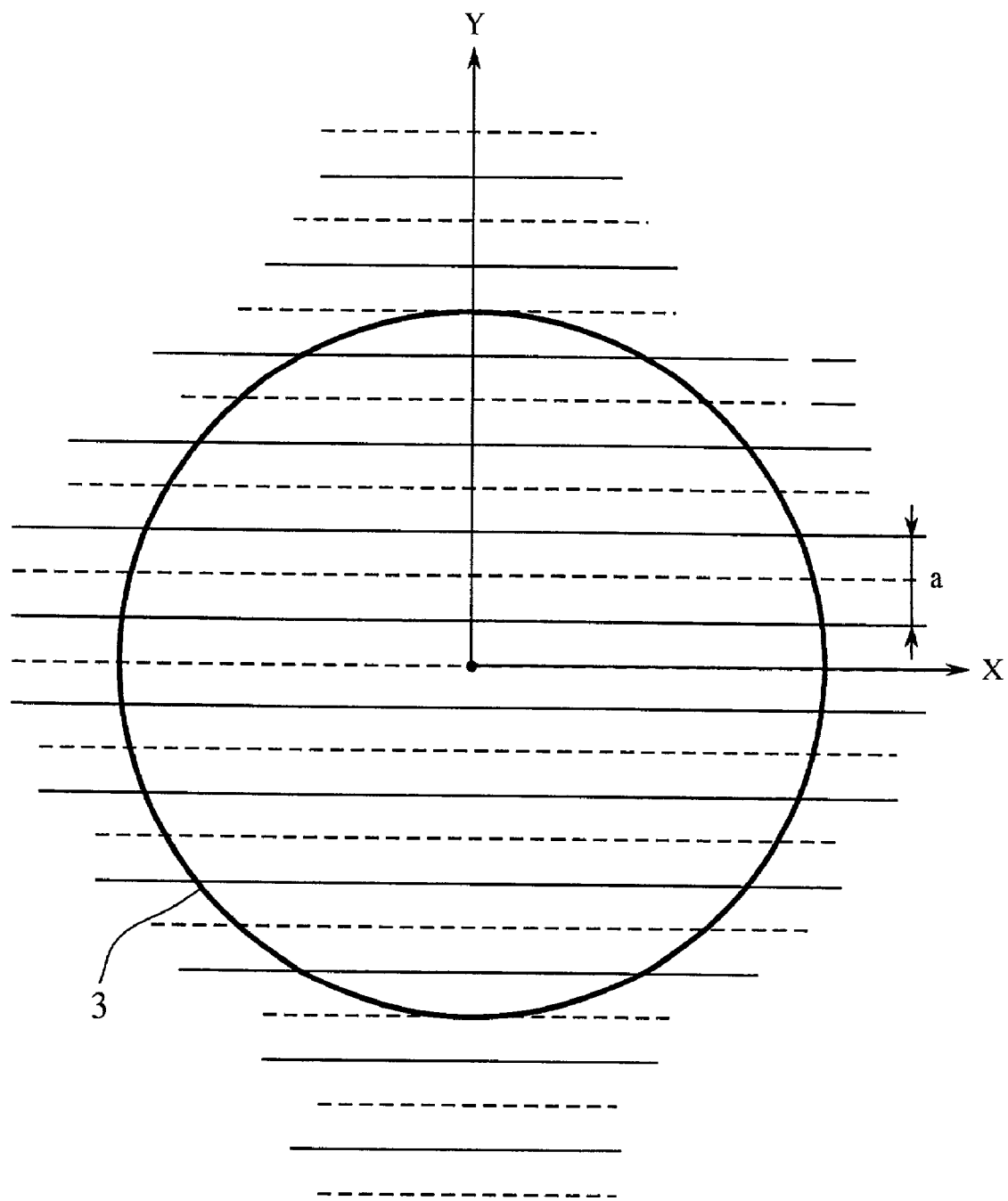
FIG. 5 is a view showing an example of division of a radiation exposure region in a radiation treatment system according to a second embodiment.

FIG. 5 shows the example of dividing the radiation exposure region in the radiation treatment system of the second embodiment. As shown, division is made such that a width a is set in parallel with an X axis from the center line of the belt region to be irradiated with particle beams, and a division range is expanded to the outside of the radiation exposure region 3. The boundary of division is given by y=ma(m=±1/2,±3/2,±5/2, . . . ). The center line for applying particle beams is given by y=ka(k=0,±1, ±2,±3, . . . ) in the broken line of FIG. 5.

Now, before the explanation of the operation of the radiation treatment system of the second embodiment, description will be made as to a condition for flattening the radiation exposure region 3 (referred to as the flattening of the radiation field, hereinafter). According to the second embodiment, it is assumed that particle beams are moved to irradiate the exposure belt-like regions with equal doses of particle beams per unit time, and the treatment planning device 4 evaluates flatness inside the radiation exposure region 3 by using the equation described above with reference to the first embodiment. However, since the equation (3) is for the movement of particle beams on a straight line, an equation (4) below is used:

$$Yj-ka$$

$$\text{but } k=0, \pm1, \pm2, \text{ and } \pm3 \ldots \quad (4)$$

In this case, similarly to the first embodiment, If it is assumed that the beam shape of particle beams is subjected to two-dimensional Gaussian distribution, then, by obtaining the integration of the equation (1) under the condition of the equation (4), a dose distribution when the equal dose of particle beams is applied along the center line can be calculated.

Figure 6:
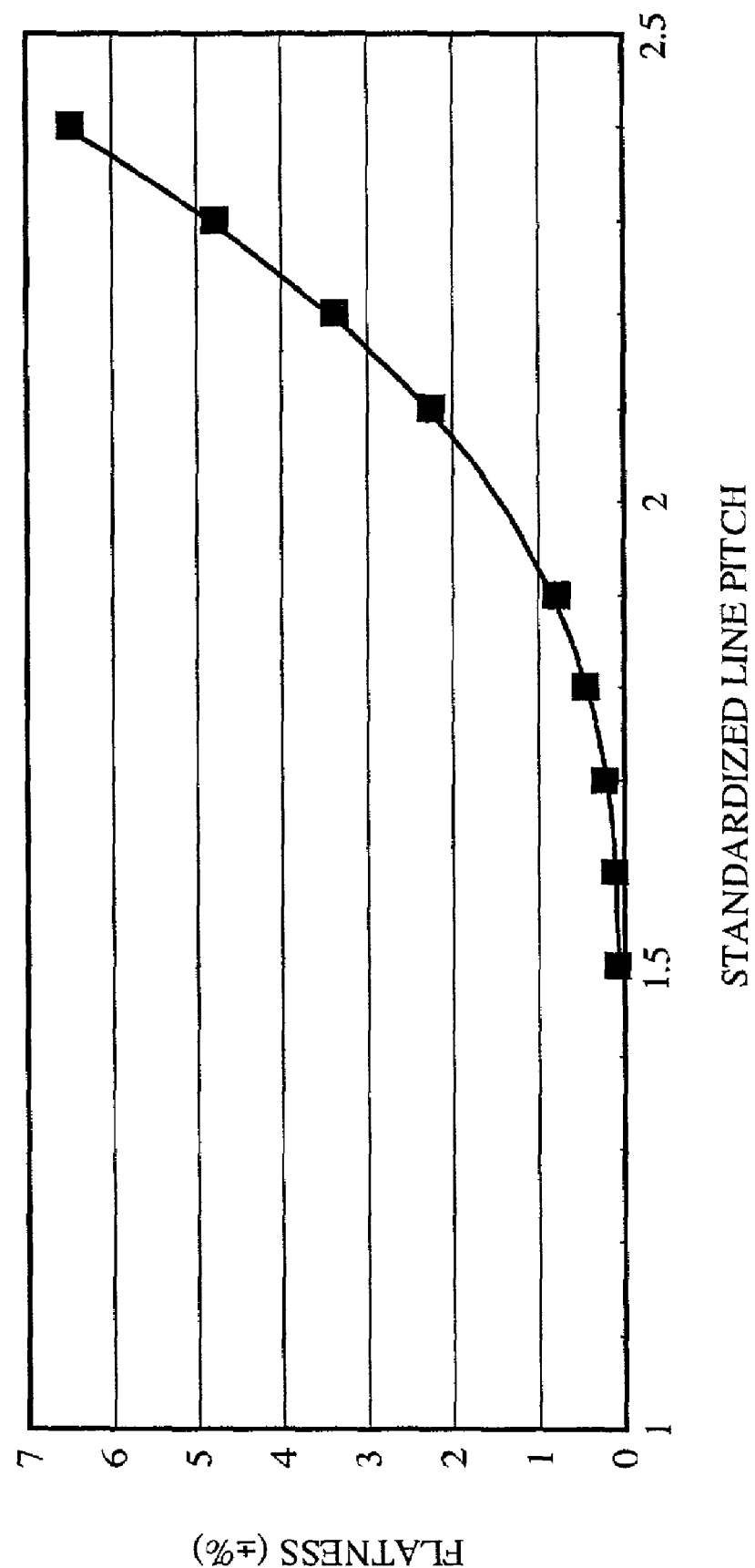
FIG. 6 is a graph showing a relation between a value of a division width a of a belt standardized by a beam shape (standard deviation $\sigma_{xy}$) and flatness according to the second embodiment.

FIG. 6 is a graph showing a relation between a value of a belt division width a standardized with a beam shape (standard deviation $\sigma_{xy}$) and flatness according to the second embodiment ($\Delta x=\Delta y$). As shown, it can be understood that the radiation exposure region 3 only needs to be divided in belt forms by the pitch of $1.9\sigma_{xy}$ in order to set the flatness of ±1%.

Figure 7:
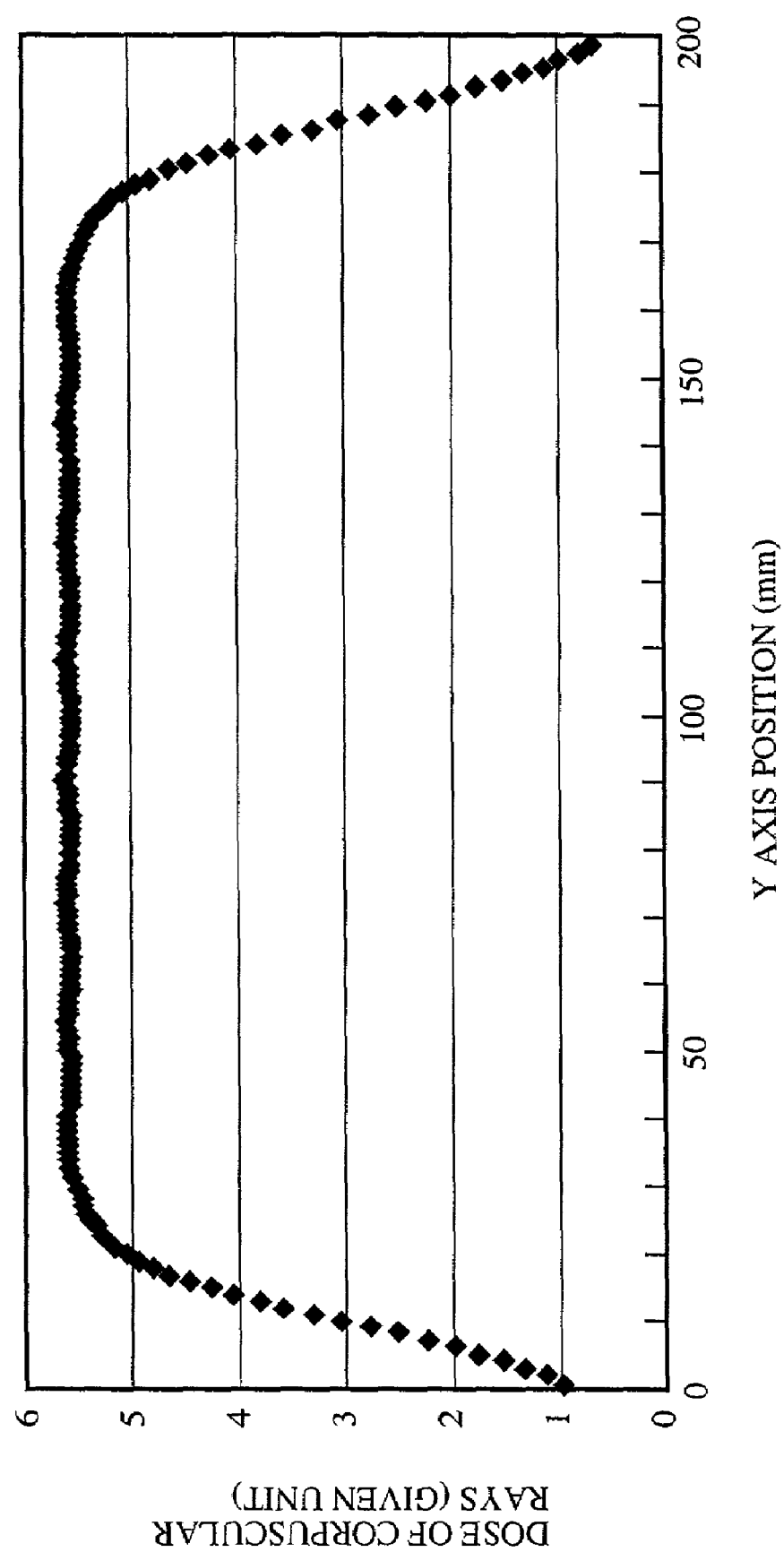
FIG. 7 is a view showing a dose distribution in a section of a direction where the radiation exposure region is divided according to the second embodiment.

FIG. 7 shows a dose distribution (amount of particle beams) in the section in the dividing direction of the radiation exposure region according to the second embodiment. A 1.9 line pitch is set when the flatness is ±1% as shown in FIG. 6. Thus, as shown in FIG. 7, when a beam shape (beam size) (standard deviation $\sigma_{xy}$) is 10 mm, the division width a of the radiation exposure region 3 becomes $1.9\sigma_{xy}$, and thus the positions of X=19, 38, and an integral multiple of 19 are irradiated with particle beams. In other words, if a beam shape $\sigma_{xy}$ is 10 mm, particle beams are scanned in the direction of X by 19 mm.

In addition, in the example shown in FIG. 7, prescribed flatness is obtained by X=38 ($2\sigma_{xy}$) to 57 ($3\sigma_{xy}$). The same applies to the center line, on which particle beams are moved. In this case, when particle beams are moved on the center line, a distance for irradiating the outside of the radiation exposure region 3 with superfluous particle beams is set equal to the width of nearly two belts. This is attributed to the fact that it is impossible to obtain desired flatness inside the radiation exposure region 3 only by a dose of particle beams from the end of the radiation exposure region 3, provided from particle beams moved on the center line of the belt of the outermost side inside the radiation exposure region 3. In other words, desired flatness is obtained by contribution of particle beams moved on the center line of the outside nearest from the end of the radiation exposure region 3 ($1.9\sigma_{xy}$) and contribution of particle beams moved on the center line located farther outside from the end of the radiation exposure region 3 ($3.8\sigma_{xy}$). On the other hand, contribution ($5.7\sigma_{xy}$) of particle beams moved on the center line of the belt located farther outside from the end of the radiation exposure region 3 becomes a size to be ignored.

Here, the irradiation with the same dose of particle beams per unit time means a condition for causing the speed of moving particle beams on the center lines of the respective belts to be equal to one another. Accordingly, loads placed on the electromagnet system for generating a magnetic field on Y axis side to move particle beams are also equal.

As for the condition for obtaining the foregoing desired flatness of the radiation field, and the number of belts in the peripheral region of the radiation exposure region 3 to be minimized (the dose of particle beams applied to the peripheral region is minimized), a specific control parameter is calculated therefor by the treatment planning device 4 during the treatment simulation.

Next, the operation of the system as configured above will now be described as below.

First, before the execution of particle-beam treatment, the diseased part (equivalent to the treatment region 1) of the patient 2 is photographed by the X-ray CT, not shown. Then, the obtained image data of the diseased part is output to the treatment planning device 4. Based on the state of the diseased part analyzed from the input image data of the diseased part, the treatment planning device 4 decides a radiation exposure region 3 by adding a region as a margin to the treatment region 1. In this case, it is assumed that in the treatment simulation carried out by the treatment planning device 4 to form a region to be irradiated with particle beams according to the second embodiment, as shown in FIG. 5, the radiation exposure region 3 and the peripheral region thereof are divided in belt forms, and an equal dose of particle beams is applied on the center line of each belt (unit radiation exposure region).

The treatment planning device 4 calculates a control parameter for applying particle beams on the center line of the belt, and outputs the control parameter to the accelerator controller 5 and the irradiation controller 6. According to the control parameter from the treatment planning device 4, the irradiation controller 6 sets leaf-control parameters for the collimator device 13 to be circumscribed on the radiation exposure region 3 assumed to be a circle having a radius r, and then controls the operations of the wobbler device 8, the scatterer device 9, the dose monitoring device 10, the ridge filter device 11, and the range shifter device 12. Associatively, the accelerator controller 5 controls the accelerator 7, generates particle beams of a beam shape decided by the interval of the belts (unit radiation exposure regions) shown in FIG. 5, and then executes treatment simulation (simulation step). Here, to apply particle beams in a belt form, the energizing current of the wobbler device 8 is controlled to generate a magnetic field for providing a deflection angle in the direction of a Y axis, equivalent to the position of the belt, and generate a magnetic field moved at a fixed speed in the direction of an X axis for moving particle beams.

In the treatment simulation carried out in the foregoing manner, at the treatment planning device 4, determination is made as to up to which of the belts located outside from the end of the radiation exposure region 3 are to be irradiated with particle beams, in order to obtain desired flatness inside the radiation exposure region 3.

In addition, in the foregoing case, no particle beams need to be applied to portions away by 3 belts or more from the end of the end of the radiation exposure region 3. Accordingly, a coordinate of the belt to be irradiated with particle beams can be calculated by the treatment simulation. Then, the treatment planning device 4 calculates the dose of particle beams to be applied according to a distance of movement on the center line of each belt.

Subsequently, by using the dose monitoring device 10, the treatment planning device 4 determines whether a dose distribution of particle beams applied according to the control parameter is appropriate or not. If the appropriate dose distribution is determined, then, the treatment planning device 4 makes a radiation treatment plan reflecting the control parameter of the belt to be irradiated with particle beams (radiation treatment planning step).

The control parameter of the radiation treatment plan is output from the treatment planning device 4 to the accelerator controller 5 and the irradiation controller 6. The accelerator controller 5 and the irradiation controller 6 set the same control parameter as that for the treatment simulation input from the treatment planning device 4 in the accelerator 7, the wobbler device 8, the scatterer device 9, the dose monitoring device 10, the ridge filter device 11, and the range shifter device 12. Further, leaf-control data corresponding to the radiation exposure region 3 is calculated, and set in the collimator device 13.

Then, the patient 2 is laid on the treatment couch 14 and fixed, and the radiation exposure region 3 is aligned with the position to be irradiated. When particle beams are applied to the radiation exposure region 3, the irradiation controller 6 controls the wobbler device 8 to set particle beams in the position corresponding to the belt to be irradiated with particle beams, sets a scatterer for providing a prescribed beam shape in the scatterer device 9, and then sets a dose of radiation rays to be applied in the dose monitoring device 10 according to the radiation treatment plan.

After the foregoing setting of the control parameter, the application of particle beams to each belt is started. When a dose monitored by the dose monitoring device 10 reaches a prescribed value (particle beams are moved by a prescribed distance), the irradiation controller 6 stops the radiation beam and performs control so as to move the particle beams to a next belt. Then, a prescribed dose is set in the dose monitoring device 10, and the irradiation with particle beams is continued (radiation exposure step). After the foregoing operation has been executed for all the belts to be irradiated with particle beams, one radiation exposure treatment is completed.

According to the second embodiment, for the flattening of the radiation field, If no particle beams are applied to the peripheral region of three belts or less from the end (boundary) of the radiation exposure region 3, flatness inside the radiation exposure region 3 cannot be secured. Consequently, a part of particle beams moved on the center line of the upper and lower two belts from the end (boundary) of the radiation exposure region 3 is wasted. In other words, assuming that the radiation exposure region 3 is a circle having a radius r, and its diameter 2r is equivalent to n belts, it is possible to approximate the number of belts necessary for flattening the radiation field by the area of a circle having a diameter (n+4), formed by adding two belts from the end of the radiation exposure region 3. The efficiency of using particle beams is given by the ratio of the number of belts in the radiation exposure region 3 and the number of belts in the region, to which the two belts of the peripheral region have been added. Thus, the efficiency is set to $(n/(n+4))^2$ considering that all the particle beams outside the radiation exposure region 3 are wasted. Therefore, it can be understood that n only needs to set equal to 5 or more to adjust the efficiency of using particle beams to 30%.

In the foregoing, the case where the radiation exposure region 3 was a circle was described. Generally, however, the radiation exposure region 3 is not a circular radiation field. Thus, in the method of the related art, the efficiency of using particle beams was lower than the theoretically value 30%. According to the second embodiment, since particle beams are applied only to the necessary belts outside the actual radiation exposure region 3, it is possible to increase the efficiency of using particle beams even if the radiation exposure region 3 is divided into the number of belts lower than five.

Moreover, in the foregoing description, the radiation exposure region 3 and the peripheral region thereof were divided in parallel with the X axis with respect to the treatment center as shown in FIG. 5. However, a similar advantage can be obtained even if the division is made in parallel with a given straight line direction.

In addition, the division was made in parallel with the X axis as shown in FIG. 5. However, a similar advantage can be obtained even if the division is made in parallel with a given curve.

In addition, the analysis was carried out assuming that the beam shape (standard deviation $\sigma_{xy}$) was isotropic as shown in FIG. 5. However, even if the beam shape is not isotropic, simulation for optimizing a stepsize can be carried out according to the beam shape, providing a similar advantage.

Further, the case where the radiation exposure region 3 was circle was described. However, a similar advantage can be obtained by carrying out simulation for applying particle beams to the region expanded by two belts outside the outermost belt in contact with the radiation exposure region 3, even if the radiation exposure region 3 has a given shape.

Furthermore, the case where the flatness of the radiation exposure region 3 was ±1% was described. However, a similar advantage can be obtained even if flatness is optionally set.

As apparent from FIG. 6, generally, the interval of the belts is smaller as the flatness of the radiation exposure region 3 is improved. As flatness is degraded, the interval of the belts is larger. If the flatness of the radiation exposure region 3 is improved, the dose of particle beams applied to the belt located outside from the end of the radiation exposure region 3 is increased. However, the dose of particle beams applied to the belt located inside the radiation exposure region 3 is also increased. On the other hand, if the flatness is degraded, the dose of particle beams applied to the belt located outside from the end of the radiation exposure region 3 is reduced. However, the dose of particle beams applied to the belt located inside the radiation exposure region 3 is also reduced.

As apparent from the foregoing relation, the efficiency of using particle beams is not so dependent on the simulated flatness, if the range of flatness used for the radiation exposure treatment is about 0.5–5%, and standard deviation $\sigma_{xy}$ of the beam shape is about 1.8–2.3.

In addition, in the example shown in FIG. 5, there was no mention of the order of irradiating the belts with particle beams. However, since the influence of the irradiating order of the belts is not so important for the formation of the radiation exposure region 3, a similar advantage can be obtained irrespective of the order of the belts facilitating the control of the wobbler device or the order facilitating control data creation.

In addition, in the example shown in FIG. 5, there was no mention of the direction of irradiating the belts with particle beams. However, since the influence of the irradiating direction of the belts is not so important for the formation of the radiation exposure region 3, a similar advantage can be obtained irrespective of the irradiating direction of the belts facilitating the control of the wobbler device 8 or the irradiating direction facilitating control data creation.

Moreover, if the contribution of the dose of particle beams applied to each belt is equal among the belts, then a similar advantage can be obtained even if scanning is carried out not just once but by a plurality of times.

In addition, in the example shown in FIG. 5, the division was made into the belts of one direction. However, a similar advantage can be obtained even if a plurality of belts divided in different directions are superposed. If the plurality of belts are superposed, the irradiating condition of each of the belts is relaxed. Examples may include a method of superposing the belts divided in the X and Y axes, a method of superposing the belts divided in the X axis and along a straight line having a given angle in the X axis, and so on.

If the dose of particle beams applied on the center line of each belt is equal, then a similar advantage is obtained even when movement is made so as to set constant the product of the speed and the number of particles of particles on each belt.

In addition, the example of division into the belts coincident with the end of the circular radiation exposure region 3 was described. However, even if the belts are not coincident with the end of the radiation exposure region 3, a similar advantage can be obtained by simulating the dose of particle beams applied to the belt located outside the radiation exposure region 3 and including the belt contributing to the radiation exposure region 3.

The example of irradiating the regularly disposed belts with the equal dose of particle beams having similar beam shapes was described. However, though calculation becomes a complex equation, even when the belts having irregular widths are irradiated with particle beams having different beam shapes, a similar advantage can be obtained if there is a solution to a reverse-problem of flattening the inside of the radiation exposure region 3.

Further, assuming that the position to be irradiated with particle beams is changed timewise, it is possible to obtain the dose of particle beams applied to each belt by the foregoing method for the actual position of each belt to be irradiated with particle beams, if there is reproducibility or regularity in such a change. On the other hand, if there is no reproducibility or regularity in the change, then it is possible to obtain the flattening condition of the radiation exposure region 3 by including the width of the change in the beam shape of particle beams to be applied.

As described above, according to the second embodiment, the radiation exposure region 3 and the peripheral region thereof to be irradiated with particle beams are divided in belt forms, the treatment simulation for applying particle beams is carried out according to each divided belt. During the execution of the treatment simulation, the radiation treatment condition is obtained for causing the flatness of the radiation exposure region 3 to be in a desired range, and the dose of particle beams applied to the belt of the peripheral region to be minimized, the radiation treatment plan reflecting the radiation treatment condition is made and, then, based on this treatment plan, particle beams are applied to the radiation exposure region 3 and the peripheral region thereof to be irradiated. Thus, since the unit radiation exposure regions obtained by dividing the radiation exposure region 3 and the peripheral region thereof into the plurality of regions are used, the radiation exposure region to be provided with desired flatness can be accurately decided, making it possible to increase the efficiency of using particle beams more compared with that in the case of the related art. Moreover, since particle beams are applied to the minimum region to be provided with desired flatness, it is possible to suppress the generation of superfluous particle beams.

Third Embodiment

The radiation treatment system of the third embodiment is basically similar in configuration to that of the first embodiment. Thus, portions different from those of the first embodiment will be described.

First, the treatment planning device 4 (simulation means and irradiation planning means) of the third embodiment forms a radiation exposure region 3 according to the state of the diseased part of the patient 2 as in the case of the first embodiment, divides the radiation exposure region 3 and the peripheral region thereof in concentric circular forms, and then sets a control parameter (radiation treatment condition) of each device for applying particle beams according to the center line of the interval of the concentric circles (unit radiation exposure region) in the accelerator controller 5 and the irradiation controller 6. The accelerator controller 5 and the irradiation controller 6 execute treatment simulation for applying particle beams according to the center line of the interval of the concentric circles divided according to the above control parameter. In the treatment simulation, the treatment planning device 4 obtains a control parameter of each device for causing the flatness of the radiation exposure region 3 to be in a desired range, and the dose of particle beams applied to peripheral region to be minimized, and then makes a radiation treatment plan reflecting this control parameter.

Similarly to the case of the first embodiment, the treatment region 1 of the third embodiment is assume to be a ball having a radius r, and the center thereof is located at the cubic center of the patient 2 assumed to be a cube having one side 4r.

Figure 8:
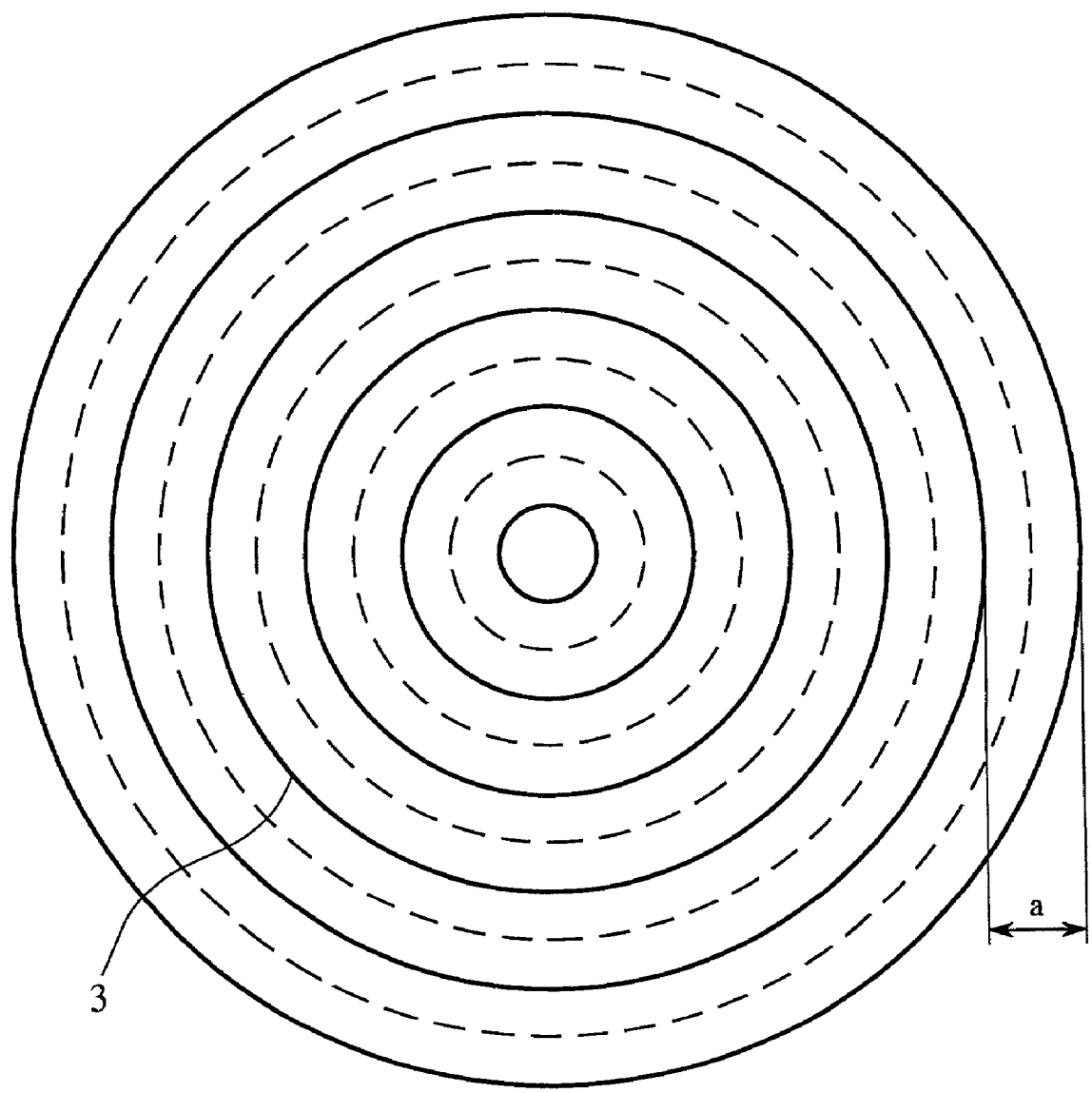
FIG. 8 is a view showing an example of division of a radiation exposure region in a radiation treatment system according to a third embodiment.

FIG. 8 shows the example of dividing a radiation exposure region in the radiation treatment system of the third embodiment. As shown, the radius of an innermost circle is increased by a/2; and the radius of an outermost circle by a. Places to be irradiated with particle beams are on circles indicated by broken lines located on the center of a concentric circle and between concentric circles, and each radius is an integral multiple of a.

Now, before the explanation of the operation of the radiation treatment system of the third embodiment, a condition for the flattening of the radiation exposure region 3 (referred to as the flattening of the radiation field, hereinafter) will be described. According to the third embodiment, assuming that particle beams are moved in such a way as to irradiate an exposure region between the concentric circles with the equal dose of particle beams per unit time, the treatment planning device 4 evaluates flatness inside the radiation exposure region 3 by using the equation described above with reference to the first embodiment. However, since the equation (3) assumes the movement of particle beams on a circle, an equation (5) below is used instead:

$$X_i^2 + Y_j^2 = (ka)^2$$

$$k = 0, 1, 2, 3 \ldots \quad (5)$$

As in the case of the first embodiment, if it is assumed that the beam shape of particle beams is subjected to two-dimensional Gaussian distribution, then, by obtaining the value of the equation (2) based on the condition of the equation (5), it is possible to calculate a dose distribution when the same dose is applied at the intervals of respective concentric circles.

For the condition of flatness, an advantage almost similar to that of the first embodiment can be expected. Accordingly, a relational equation can be obtained between the beam shape and the radius of the concentric circle according to flatness.

As in the case of each of the first and second embodiments, if a relation between the interval of the concentric circles standardized by the beam shape (standard deviation $\sigma_{xy}$) and flatness is assumed, then particle beams must be applied at the interval of at least two concentric circles outside the radiation exposure region 3.

This is attributed to the fact that only by the dose from the end of the radiation exposure region 3, provided from particle beams moved on the outermost concentric circle inside the radiation exposure region 3, it is impossible to obtain desired flatness in the radiation exposure region 3. In other words, desired flatness can be obtained by contribution ($1.9\sigma_{xy}$) of particle beams on the concentric circle rotated in the nearest outside from the end of the radiation exposure region 3, and contribution ($3.8\sigma_{xy}$) of particle beams on the concentric circle rotated in the outside farther separated away from the end of the radiation exposure region 3. On the other hand, contribution ($5.7\sigma_{xy}$) of particle beams rotated on the concentric circle located in the outside yet farther separated away from the end of the radiation exposure region 3 becomes a size to be ignored.

In this case, the application of the equal dose of particle beams per unit time means a condition for causing the moving speeds of particle beams on the concentric circles to be equal to one another. Accordingly, the rotational time of particle beams applied to the concentric circle of the outside is lengthened, making it possible to reduce a frequency for rotating particle beams in inverse proportion to the rotational radius.

As for the condition for obtaining the desired flatness of the radiation field, and minimizing the number of concentric circles in the peripheral region of the radiation exposure region 3 (minimizing the dose of particle beams applied to the peripheral region), a specific control parameter therefor is calculated by the treatment planning device 4 during the treatment simulation.

Next, the operation of the system as configured above will now be described as below.

First, before the execution of particle-beam treatment, the diseased part (equivalent to the treatment region 1) of the patient 2 is photographed by the X-ray CT, not shown, and the obtained image data of the diseased part is output to the treatment planning device 4. Based on the state of the diseased part analyzed from the input image data of the diseased part, the treatment planning device 4 decides a radiation exposure region 3 by adding a region as a margin to the treatment region 1. In this case, it is assumed that in the treatment simulation for forming the region to be irradiated with particle beams, carried out at the treatment planning device 4 according to the third embodiment, as shown in FIG. 8, the radiation exposure region 3 and the peripheral region thereof are divided in concentric circular forms, and the equal dose of particle beams is applied on the center line at the interval (unit radiation exposure region) of the concentric circles.

The treatment planning device 4 calculates a control parameter for applying particle beams on the center line at the interval of the concentric circles, and then outputs the control parameter to the accelerator controller 5 and the irradiation controller 6. Based on the control parameter input from the treatment plan device 4, the irradiation controller 6 sets leaf-control parameters for the collimator device 13 to be circumscribed on the radiation exposure region 3 assumed to be a circle having a radius r, and controls the movements of the wobbler device 8, the scatterer device 9, the dose monitoring device 10, the ridge filter device 11, and the range shifter device 12. Associatively, the accelerator controller 5 controls the accelerator 7, generates particle beams having a beam shape decided by the interval of the concentric circles shown in FIG. 8, and then executes treatment simulation (simulation step). In this case, to apply particle beams in a concentric circular form, the energizing current of the wobbler device 8 is controlled, and a rotational magnetic field for providing a prescribed angle of deflection to particle beams is generated.

In the treatment simulation carried out in the foregoing manner, the treatment planning device 4 determines which of the concentric circles located in the outside from the end of the radiation exposure region 3 is irradiated with particle beams, in order to obtain desired flatness inside the radiation exposure region 3.

Moreover, in the foregoing case, no particle beams need to be applied to a portion located away by three concentric circles or more from the end of the radiation exposure region 3. Thus, a coordinate of the concentric circle to be irradiated with particle beams can be obtained by the treatment simulation. Then, the treatment planning device 4 calculates a frequency of particle beams when one rotation is made on each concentric circle, and the dose of particle beams to be applied by one rotation.

Subsequently, by using the dose monitoring device 10, the treatment planning device 4 determines whether the dose distribution of the particle beams applied according to the control parameter is appropriate or not. If the appropriate dose is determined, then, the treatment planning device 4 makes a radiation treatment plan reflecting the control parameter of the concentric circle to be irradiated with particle beams (radiation treatment planning step).

The control parameter of the above radiation treatment plan is output from the treatment planning device 4 to the accelerator controller 5 and the irradiation controller 6. The accelerator controller 5 and the irradiation controller 6 set the same control parameter as that of the treatment simulation input from the treatment planning device 4 in the accelerator 7, the wobbler device 8, the scatterer device 9, the dose monitoring device 10, the ridge filter device 11, and the range shifter device 12. In addition, leaf control data corresponding to the radiation exposure region 3 is calculated, and set in the collimator device 13.

Subsequently, the patient 2 is laid on the treatment couch 4 and fixed, and the radiation exposure region 3 is aligned with the radiation exposure position. When the radiation exposure region 3 is irradiated with particle beams, the irradiation controller 6 controls the wobbler device 8 to set particle beams in the position corresponding to the concentric circle to be irradiated with particle beams, sets a scatterer for providing a prescribed beam shape in the scatterer device 9, and then sets the dose of particle beams to be applied in the dose monitoring device 10 according to the radiation treatment plan.

After the setting of the control parameter in the foregoing manner, the application of particle beams at the interval of the concentric circles is started. When the dose of particle beams monitored by the dose monitoring device 10 reaches a prescribed value (particle beams make one rotation), the irradiation controller 6 stops the radiation beam, and performs control to move the particle beams to a next concentric circle, and then the application of the particle beams is continued (radiation exposure step). After the foregoing operation has been carried out for all the intervals of the concentric circles, one radiation exposure treatment is completed.

According to the third embodiment, for the flattening of the radiation field, if no particle beams are applied to the peripheral region within the interval of three concentric circles or less from the end (boundary) of the radiation exposure region 3, flatness inside the radiation exposure region 3 cannot be secured. Therefore, a part of particle beams applied to the interval of two concentric circles from the end (boundary) of the radiation exposure region 3 is wasted.

In other words, assuming that the radiation exposure region 3 is a circle having a radius r, and its diameter 2r is equivalent to n concentric circles, it is possible to approximate the number of the intervals of concentric circles necessary for the flattening of the radiation field by the area of a circle having a diameter (n+4), formed by adding the interval of two concentric circles from the end of the radiation exposure region 3. The efficiency of using particle beams is given by the ratio of the number of concentric circles in the radiation exposure region 3, and the number of concentric circles in the region obtained by adding two concentric circles of the peripheral region to the radiation exposure region 3. Thus, the efficiency is given by $(n/(n+4))^2$, considering that all the particle beams outside the radiation exposure region 3 are wasted. Therefore, it can be understood that to adjust the efficiency of using particle beams to 30%, n must be increased to 5 or more.

Moreover, in the foregoing, the case where the radiation exposure region 3 was a circle was described. Generally, however, the radiation exposure region 3 is not a circular radiation field. Therefore, the efficiency of using particle beams was lower than the theoretical value 30% in the method of the related art. According to the third embodiment, by making division in a flat concentric elliptic form according to the actual radiation exposure region 3, it is possible to increase the actual efficiency of using particle beams even if the radiation exposure region 3 is divided into five concentric ellipse or higher.

Moreover, in the foregoing, the case where the radiation exposure region 3 and the peripheral region thereof were divided in the odd number of concentric circles so as to move the particle beams on the boundary of the radiation exposure region 3 as shown in FIG. 8. However, a similar advantage can be obtained by setting the even number of divided regions so as to prevent the movement of the particle beams on the boundary of the radiation exposure region 3, passing the middle part between radiation beams on the boundary.

In addition, in the foregoing, the example of division into the concentric circles was described. However, a similar advantage can be obtained even if division is made into given concentric ellipses.

In addition, the analysis was carried out assuming that the beam shape (standard deviation $\sigma_{xy}$) was isotropic as shown in FIG. 8. However, even if the beam shape is not isotropic, simulation for optimizing a stepsize according to the beam shape can be performed, proving a similar advantage.

The case where the radiation exposure region 3 was a circle was described. However, a similar advantage can be obtained by executing simulation for applying particle beams to the region expanded by two concentric circles outside the outermost concentric circle in contact with the radiation exposure region 3, even for the radiation exposure region 3 having a given shape.

In addition, the case where the flatness of the radiation exposure region 3 was ±1% was described. However, a similar advantage can be obtained even for given flatness.

Generally, the interval of the concentric circles is smaller as the flatness of the radiation exposure region 3 is improved. The interval of the concentric circles is larger as the flatness is degraded. By improving the flatness of the radiation exposure region 3, the dose of particle beams applied to the concentric circle located outside from the end of the radiation exposure region 3 is increased. However, the dose of particle beams applied to the concentric circle located inside the radiation exposure region 3 is also increased. On the other hand, if the flatness is degraded, the dose of particle beams applied to the concentric circle located outside from the end of the radiation exposure region 3 is reduced. However the dose of particle beams applied to the concentric circle located inside the radiation exposure region 3 is also reduced.

Apparently from the foregoing relation, the efficiency of using particle beams is not so dependent on the simulated flatness if the range of flatness used for the radiation exposure treatment is about 0.5–5%, and the standard deviation $\sigma_{xy}$ of the beam shape is about 1.7–2.1.

Further, in the example shown in FIG. 8, there was no mention of the order of irradiating the interval of the concentric circles with particle beams. However, since the influence of the irradiating order of the concentric circles is not so important for the formation of the radiation exposure region 3, a similar advantage can be obtained irrespective of the irradiating order of the concentric circles facilitating the control of the wobbler device 8 or the irradiating order facilitating control data creation.

In the foregoing, the center portion was not wobbled. However, even when the center portion is wobbled as in the case of the method of the related art, a similar advantage can be obtained by carrying out similar simulation.

Moreover, if the contribution of the dose of particle beams is similar among the concentric circles, then a similar advantage can be obtained even when rotation is made not just once but by a plurality of times.

If the dose of particle beams is equal among the concentric circles, then a similar advantage can be obtained even when movement is made so as to set constant the product of the speed of particle beams and the number of particle beams.

The example where the concentric circles were regularly disposed, and the same dose of particle beams having similar beam shapes were applied in each concentric circle was described. However, though calculation becomes a complex equation, even when particle beams having different beam sizes are applied to the irregularly disposed concentric circles, a similar advantage can be obtained if there is a solution to a reverse-problem for flattening the inside of the radiation exposure region 3.

In addition, assuming that the position to be irradiated with particle beams is changed timewise, if there is reproducibility or regularity of such a change, then it is possible to calculate the dose of particle beams applied to the position by the foregoing method. On the other hand, if there is not reproducibility or regularity of the change, then it is possible to obtain the flattening condition of the radiation exposure region 3 by including the width of the change in the beam size of particle beams to be applied.

As described above, according to the third embodiment, the radiation exposure region 3 and the peripheral region thereof to be irradiated with particle beams are divided in the concentric circular forms, the treatment simulation is executed according to the interval of the divided concentric circles. During the treatment simulation, the radiation treatment condition is obtained for causing the flatness of the radiation exposure region 3 to be in a desired range, and the dose of particle beams applied to the interval of the concentric circles of the peripheral region to be minimized, the radiation treatment plan reflecting this radiation treatment condition is made and, based on the radiation treatment plan, the radiation exposure region 3 and the peripheral region thereof are irradiated with particle beams. Thus, since the unit radiation exposure regions obtained by dividing the radiation exposure region 3 and the peripheral region into the plurality of regions, it is possible to accurately decide the radiation exposure region for providing desired flatness, and to increase the efficiency of using particle beams more compared with the case of the related art. Moreover, since particle beams are applied to the interval of the concentric circles of the minimum peripheral region for providing desired flatness, it is possible to suppress the generation of superfluous particle beams.

It is necessary to supply much more current to the wobbler device 8 when particle beams are rotated outside. However, if rotation is made so as to set constant the dose of particle beams applied to each concentric circle, the frequency of the concentric circle outside is reduced in inverse proportion to the rotational radius, lowering a power supply load or the like on the wobbler device 8. Thus, it is possible to facilitate system configuration.

As described heretofore, according to the present invention, the radiation exposure region and the peripheral region thereof are divided into a plurality of unit exposure regions, and the radiation treatment simulation is executed for applying particle beams according to the shape of each divided unit radiation exposure region. During the radiation treatment simulation, the radiation treatment condition is obtained for causing the flatness, i.e., the degree of uniformly irradiating the radiation exposure region with a proper dose of particle beams, to be in a desired range, and the dose of particle beams applied to the unit radiation exposure region of the peripheral region to be minimized, and then the radiation treatment plan reflecting this radiation treatment condition is made. Thus, it is possible to accurately decide the radiation exposure region for providing desired flatness, and to increase the efficiency of using particle beams more compared with the case of the relate art. Moreover, since particle beams are applied to the minimum peripheral region for providing desired flatness, it is possible to suppress the generation of superfluous particle beams.

According to this invention, the radiation exposure region and the peripheral region thereof are divided into the unit radiation exposure regions of the grid form. Thus, it is possible to accurately decide the radiation exposure region for providing desired flatness.

According to the invention, the radiation exposure region and the peripheral region thereof are divided into the belt-like unit exposure regions. Thus, an advantage similar to the above can be obtained by the foregoing method.

According to the invention, since the radiation exposure region and the peripheral region thereof are divided into the concentric circular unit exposure regions, an advantage similar to the above can be obtained by the foregoing method. Moreover, since rotation is made so as to set constant the dose of particle beams applied to each concentric circle, the frequency of the concentric circle outside is reduced in inverse proportion to the rotational radius. Therefore, it is possible to reduce a power supply load or the like on the wobbler device.

Furthermore, according to the invention, when the unit exposure region is located in the boundary of the radiation exposure region, determination is made as to the degree of contribution made by the dose of particle beams applied to the unit exposure region located in the boundary to the radiation exposure region, according to the dose of particle beams applied to the unit exposure region located in the boundary of the peripheral region. Thus, it is possible to suppress the generation of superfluous particle beams.

What is claimed is:

1. A radiation treatment plan making system comprising:
simulation means for executing radiation treatment simulation for dividing a radiation exposure region and a peripheral region thereof to be irradiated with particle beams into a plurality of unit radiation exposure regions, and then applying particle beams according to a shape of each divided unit radiation exposure region; and radiation treatment planning means for obtaining a radiation treatment condition for causing flatness, which is a degree of uniformly irradiating the radiation exposure region with a proper dose of particle beams, to be in a desired range, and a dose of particle beams applied to the unit radiation exposure region of the peripheral region to be minimized, in the case where the simulation means executes the radiation treatment simulation, and then making a radiation treatment plan reflecting the radiation treatment condition, wherein the simulation means divides the radiation exposure region and the peripheral region thereof into unit radiation exposure regions of grid forms whose size is set according to a radiation beam size that is decided by an operation condition, which decides the flatness, of the radiation treatment apparatus, and performs radiation treatment simulation that simulates operation for applying radiation treatment for the unit radiation exposure regions with a pitch of one half of one side of the grid as a step size, and wherein the radiation treatment planning means determines a degree of contribution made by a dose of radiation on the flatness of radiation exposure region at the unit radiation exposure region simulated on the peripheral region based on the dose of radiation at the radiation beam size simulated by the radiation treatment simulation, and based on the result of this determination, the radiation treatment planning means obtains an operation condition for the radiation treatment apparatus as the radiation treatment condition in which the peripheral regions that satisfy the desired flatness in the radiation exposure region, and whose number of grid becomes minimum to obtain the flatness.

2. A radiation treatment plan making method comprising:
simulation for dividing a radiation exposure region and a peripheral region thereof to be irradiated with particle beams into a plurality of unit radiation exposure regions, and then executing radiation treatment simulation according to a shape of each divided unit radiation exposure region; and radiation treatment planning of obtaining a radiation treatment condition for causing flatness, which is a degree of uniformly irradiating the radiation exposure region with a proper dose of particle beams, to be in a desired range, and a dose of particle beams applied to the unit radiation exposure region of the peripheral region to be minimized, in the case where the simulation is executed, and then making a radiation treatment plan reflecting the radiation treatment condition, wherein in the simulation, the radiation exposure region and the peripheral region thereof are divided into unit radiation exposure regions of grid forms whose size is set according to a radiation beam size that is decided by an operation condition, which decides the flatness, of the radiation treatment apparatus, and radiation treatment simulation that simulates operation for applying radiation treatment for the unit radiation exposure regions is performed with a pitch of one half of one side of the grid as a step size, and wherein in the radiation treatment planning, a degree of contribution made by a dose of radiation on the flatness of radiation exposure region at the unit radiation exposure region simulated on the peripheral region based on the dose of radiation at the radiation beam size simulated by the radiation treatment simulation, is determined and based on the result of this determination, in the radiation treatment planning, an operation condition for the radiation treatment apparatus is obtained as the radiation treatment condition in which the peripheral regions that satisfy the desired flatness in the radiation exposure region, and whose number of grid becomes minimum to obtain the flatness.

* * * * *